United States Patent [19]
Jäger et al.

[11] 4,062,875
[45] Dec. 13, 1977

[54] PREPARATION AND OXIDATION OF 4-ACYLAMINO-ANTHRONES

[75] Inventors: Horst Jäger, Leverkusen; Erich Klauke, Odenthal, both of Germany

[73] Assignee: Bayer Aktiengesellschaft, Leverkusen, Germany

[21] Appl. No.: 659,601

[22] Filed: Feb. 19, 1976

[30] Foreign Application Priority Data

Mar. 8, 1975    Germany ............................. 2510260

[51] Int. Cl.$^2$ .......................... C07C 63/44; C09B 1/00
[52] U.S. Cl. ..................................... 260/351; 260/377
[58] Field of Search ................................ 260/377, 351

[56] References Cited

U.S. PATENT DOCUMENTS

| | | | |
|---|---|---|---|
| 1,906,581 | 5/1933 | Gubelmann et al. | 260/351 |
| 1,916,216 | 7/1933 | Gubelmann et al. | 260/351 |
| 3,835,167 | 9/1974 | Pfister | 260/351 |

FOREIGN PATENT DOCUMENTS

| | | | |
|---|---|---|---|
| 594,168 | 2/1934 | Germany | 260/351 UX |

OTHER PUBLICATIONS

Lubs, "The Chemistry of Synthetic Dyes and Pigments," Hafner Publishing Co., N.Y. (1955), p. 342.

*Primary Examiner*—Paul F. Shaver
*Attorney, Agent, or Firm*—Burgess, Dinklage & Sprung

[57] ABSTRACT

A 2-acylamino-2'-carboxy-diphenylmethane is treated with an acid condensing agent such as sulfuric acid or chlorosulfonic acid thereby to produce the corresponding 4-acylamino-anthrone which can then be oxidized, as with hydrogen peroxide or oxygen, to the corresponding 1-acylamino-anthraquinone.

13 Claims, No Drawings

PREPARATION AND OXIDATION OF 4-ACYLAMINO-ANTHRONES

The present invention relates to a process for the preparation of 4-acylamino-anthrones from 2-acylamino-2'-carboxy-diphenylmethanes and their further processing to acylaminoanthraquinones.

Formyl- and acetyl-amino-anthrone are known from German Pat. No. 594,168. They are prepared by reacting 4-aminoanthrone with formic acid or, respectively, acetic anhydride.

It has now been found that 4-acylamino-anthrones are obtained quite generally in a technically advantageous manner when 2-acylamino-2'-carboxy-diphenylmethanes are treated with an acid condensing agent.

This was surprising insofar as it was to be seen from German Pat. No. 594,168 that the treatment of 2-formylamino-2'-benzylbenzoic acid with phosphorus oxychloride leads to a pyrrolanthrone.

2-Acylamino-2'-carboxy-diphenylmethanes are in themselves known; for example German Pat. No. 594,168 describes the preparation of 2-formylamino-2'carboxy-diphenylmethane by heating 2'-amino-2-benzylbenzoic acid with formic acid. In general, the 2-acylamino-2'-carboxy-diphenylmethanes which can be employed according to the invention are obtained by acylation of 2-amino-2'-carboxy-diphenylmethane in a manner which is in itself known with, for example, the acid chlorides or the anhydrides of the particular acids. Only when introducing the carbamoyl radical is the procedure advantageously modified so that 2-amino-2'-carboxy-diphenylmethane is reacted with potassium cyanate in a manner which is in itself known. 2-Amino-2'-carboxy-diphenylmethane is in itself known and its preparation is described, for example, in German Pat. No. 553,001 [1930, Friedländer 19, 1978].

Starting materials which can be used for the process according to the invention are 2-acylamino-2'-carboxy-diphenylmethanes, the acyl radicals of which are derived from aliphatic, cycloaliphatic, araliphatic and aromatic carboxylic acids and from aromatic and aliphatic sulfonic acids. Possible aliphatic carboxylic acids are, in general, straight-chain or branched and have up to 18 carbon atoms, preferably 2 to 5 carbon atoms. Examples which may be mentioned are acetic acid, propionic acid, butanoic acid, isovaleric acid, pivalic acid and stearic acid.

In the case of the cycloaliphatic carboxylic acids, possible acids are, for example, those with 6 to 11 carbon atoms. Examples which may be mentioned are cyclohexanecarboxylic acid and decalincarboxylic acid, cyclohexanecarboxylic acid preferably being employed.

Possible araliphatic acyl radicals are acyl radicals of araliphatic carboxylic acids with 8 to 10 C atoms. Examples which may be mentioned are the radicals of phenylacetic acid, tolylacetic acid, phenylpropionic acid and phenoxyacetic acid. The radical of phenylacetic acid is preferred.

Possible acyl radicals of aromatic carboxylic acids are acyl radicals of aromatic carboxylic acids with up to 3 fused benzene nuclei, which are optionally substituted by halogen, nitro, sulfo, alkyl or alkoxy. Examples which may be mentioned are the radicals of benzoic acid, p-chlorobenzoic acid, 4-methyl-benzoic acid, 3-sulfobenzoic acid, 4-methoxybenzoic acid, 3-nitrobenzoic acid, naphthalene-1-carboxylic acid, naphthalene-2-carboxylic acid, anthraquinone-1-carboxylic acid, anthraquinone-2-carboxylic acid and diphenylcarboxylic acid.

Examples of radicals of aromatic and aliphatic sulfonic acids which may be mentioned are the radicals of methanesulfonic acid, ethanesulfonic acid, butanesulfonic acid, benzenesulfonic acid, p-chlorobenzenesulfonic acid, p-tolylsulfonic acid and naphthalenesulfonic acid.

Examples of possible acyl radicals which may be mentioned individually are: formyl, acetyl, propionyl, acryloyl, butyryl, acetoacetyl, valeroyl, monochloroacetyl, cyclohexanecarbonyl, phenylacetyl, benzoyl, p-chlorobenzoyl, m-nitrobenzoyl, methanesulfonyl, p-tolylsulfonyl, cyano, carbamoyl, methoxycarbonyl, phenoxycarbonyl, dimethylcarbamoyl, ethoxycarbonyl, oxalyl and o-carboxybenzoyl.

Acetyl and benzoyl are preferably employed.

Examples which may be mentioned of acid condensing agents according to the process of the invention are: sulfuric acid, chlorosulfonic acid, fluorosulfonic acid, polyphosphoric acid, fluoroalkylsulfonic acids, containing up to about 8 carbon atoms, such as, for example, perfluorobutanesulfonic acid, and hydrofluoric acid.

Sulfuric acid, chlorosulfonic acid and fluorosulfonic acid are preferably employed, the use of sulfuric acid being particularly preferred; sulfuric acid is employed in concentrations of about 75 to 110%, preferably about 95 to 100%.

The amount of condensing agent employed can vary within wide limits. In general, about the 2-fold to 10-fold amount by weight, relative to the particular 2-acylamino-2'-carboxydiphenylmethane, can be employed. When sulfuric acid is used as the condensing agent, preferably about the 3-fold to 6-fold amount by weight is employed.

In general, the procedure according to the process of the invention is such that the acid condensing agent is initially introduced and the particular 2-acylamino-2'-carboxydiphenylmethane is introduced while stirring, care being taken that the temperature of the mixture does not rise above about 40° C during the introduction. The mixture is left at the particular reaction temperature for a time, generally 0.1 to 10 hours. In order to isolate the reaction product, the reaction mixture can generally be discharged onto an ice/water mixture and the precipitate filtered off. The residue on the filter is washed with water until neutral and dried.

The reaction temperatures can vary within wide limits and are generally between 0° and 100° C, preferably between about 0° and 60° C. In particular, temperatures of about 5° to 40° C are preferred. When sulfuric acid is used as the condensing agent, the reaction can generally be carried out at 20° to 40° C. When chlorosufonic acid is used, on the other hand, the reaction can in general be carried out at about 0° to 20° C.

The 4-acylamino-anthrones obtained according to the invention are intermediates for the advantageous preparation of 1-acyl-aminoanthraquinones.

The procedure for this can be that the particular 4-acylaminoanthrone is dissolved or suspended in water, sulfuric acid, water/sulfuric acid, a solvent or a water/solvent mixture, and oxidized.

The oxidation can be carried out both in an acid and in an alkaline medium, oxidation in an alkaline medium being preferred. Agents to be added, if appropriate, in order to adjust the alkalinity, are hydroxides, oxides, carbonates, bicarbonates, borates, aluminates, silicates and phosphates of the alkali metal and/or alkaline earth metals. The addition of ammonia or its alkyl or aralkyl compounds is also possible. Examples of individual compounds which may be mentioned are: sodium hydroxide, potassium hydroxide, sodium carbonate, potassium carbonate, magnesium hydroxide, calcium hydroxide, trisodium phosphate, sodium water glass and potassium water glass.

The amount of alkaline compound added can vary within wide limits and in general these compounds can be added in the 0.05-fold to 10-fold amount, relative to the 4-acylaminoanthrone employed, addition in 0.1 to 1 times the equimolar amount being preferred.

Possible oxidizing agents are all known oxidizing agents and examples which may be mentioned are: chlorine, bromine, sodium hypochlorite, air, oxygen, hydrogen peroxide, perborates, peroxymonosulfates, peroxydisulfates, peroxymolybdates, peroxytungstates, vanadates, potassium permanganate, manganese dioxide, potassium dichromate, sodium chromate, nitric acid and sulfur trioxide. The oxidizing agent is generally employed in an equivalent amount, it also being possible, without disadvantage to use an excess of the oxidizing agent. Preferred oxidizing agents are air and hydrogen peroxide in an alkaline medium. Oxidation with hydrogen peroxide in the aqueous phase with addition of sodium water glass and potassium water glass, or with air or pure oxygen in the alcoholic phase and in the presence of alkaline agents, for example sodium carbonate or potassium carbonate, is particularly preferred. Possible solvents to be employed if appropriate are alcohols, ketones, organic acids, hydrocarbons and chlorinated hydrocarbons. Examples which may be mentioned are methanol, ethanol, isopropanol, acetone, methyl ethyl ketone, methyl isopropyl ketone, cyclohexanone, acetic acid, propionic acid, benzene, toluene, xylene, methylene chloride, chloroform, carbon tetrachloride, chlorobenzene and dichlorobenzene.

The oxidation can generally be carried out at temperatures of from 0° to 100° C, preferably 20° to 80° C.

1-Acylamino-anthraquinones can themselves be employed as a dyestuff, examples being 1-benzoylaminoanthraquinone (Algol Yellow WG; Beilstein, volume XIV, supplement II, page 103); and 1-(4'-phenylbenzoyl)-amino-anthraquinone (Anthrasol Yellow V, Leuko-sulphuric acid ester; Ullmann, Encyclopaedie der technischen Chemie (Encyclopedia of Industrial Chemistry), volume 3, page 699, 3rd edition). Furthermore, their saponification product, that is 1-aminoanthraquinone, which is obtained in a manner which is in itself known, is a valuable intermediate for a large number of dyestuffs (Ullmann, Encyclopaedie der technischen Chemie (Encyclopedia of Industrial Chemistry), volume 3, page 730, 3rd edition).

The invention is further described in the following illustrative examples wherein all parts are by weight unless otherwise expressed.

EXAMPLE 1

134.5 g of 2-acetylamino-2'-carboxy-diphenylmethane (0.5 mole) are introduced into 340 ml of 100% strength sulfuric acid and, by means of cooling, the temperature is not allowed to rise above 40° C. The mixture is then warmed to 40° C for 3 hours, a dark green solution being obtained. For isolation, the mixture is discharged at 20° onto a mixture of 770 g of ice and water. After stirring briefly, the mixture is filtered. The sulfuric acid content in the filtrate is 43–44%. In order to remove the mother liquor, the residue is washed several times with small amounts of water until neutral. After drying, 123 g of 4-acetamino-anthrone are obtained.

Yield: 98%/melting point 268°–271° C.

EXAMPLE 2

134.5 g of 2-acetylamino-2'-carboxy (0.5 mole) are introduced into 300 ml of 100% strength sulfuric acid and, by means of cooling, the temperature is not allowed to rise above 40° C. The mixture is then warmed to 40° C. for 3 hours, a dark green solution being formed. In order to precipitate the reaction product, the mixture is discharged at 20° C onto a mixture of 680 g of ice and water. After stirring briefly, the mixture is filtered. The sulfuric acid content of the filtrate is 43–44%. In order to remove the adhering mother liquor, the residue is washed several times with small amounts of water until neutral. After drying, 120 g of 4-acetaminoanthrone are obtained.

Yield: 91.6% / melting point 268°–271° C.

EXAMPLE 3

When the following 2-acylamino-2'-carboxy-diphenylmethanes are employed and the procedure according to instructions in Example 1 is followed, the corresponding 4-acylaminoanthrones, listed in the table which follows, are obtained, again in virtually quantitative yield.

|  |  | Melting point (° C) |
|---|---|---|
| 2-Benzoylamino-2'-carboxy-diphenylmethane | 4-Benzoylamino-anthrone | 239 – 244 |
| 2-Carbamoylamino-2'-carboxy-diphenylmethane | 4-Carbamoylamino-anthrone | 284 – 288 |
| 2-Methoxycarbonylamino-2'-carboxydiphenylmethane | 4-Methoxycarbonyl-aminoanthrone | 216 – 217 |

EXAMPLE 4

134.5 g of 2-acetylamino-2'-carboxyl-diphenylmethane (0.5 mole) are introduced into 260 ml of 100% strength sulfuric acid and, by means of cooling, the temperature is not allowed to rise above 30° C. The mixture is then warmed to 30° C for 6 hours, a dark green solution being formed. For isolation, the mixture is discharged at 20° C onto a mixture of 570 g of ice and water. After stirring briefly, the mixture is filtered. The sulfuric acid content of the filtrate is 43%. In order to remove the bulk of the sulfuric acid, the residue is washed several times with small amounts of water. The paste is then introduced into 500 ml of water, while stirring, and the pH value of the mixture is adjusted to 8 with 10% strength sodium carbonate solution. The mixture is again filtered and the residue is washed once with water. After drying, 113 g of 4-acetamino-anthrone are obtained.

Yield: 90% / melting point 266° C.

EXAMPLE 5

26.9 g of 2-acetylamino-2'-carboxy-diphenylmethane are introduced into 40 ml of chlorosulfonic acid in the course of 20 minutes at 0° to 5° C. The mixture is stirred for a further 3 hours at 0° to 5° C and is then discharged onto ice. After stirring briefly, the mixture is filtered and the residue is washed until neutral. After drying at 50° to 70° C, 22.4 g of 4-acetamino-anthrone are obtained.

Yield: 89.2% / melting point 268° C.

EXAMPLE 6

125.5 g (0.5 mole) of 4-acetamino-anthrone in 1.5 liters of water are warmed to 70°. 50 ml of sodium water glass are added ($d = 1.35$) and 400 ml of a hydrogen peroxide solution which contains 80 g of $H_2O_2$ per liter are then allowed to run in dropwise in the course of 1 hour. Appropriately, a slight stream of nitrogen is passed over the surface during the reaction. The mixture is then stirred at between 70° and 90° C until no further starting material is found in a sample which is withdrawn and examined by thin layer chromatography. In the course of the oxidation, the suspension has developed an intense yellow color. The suspension is filtered and the product washed until neutral. After drying, 125 g of 1-acetamino-anthraquinone with a melting point of 221° C are obtained.

Yield: 94.3%.

EXAMPLE 7

135.5 g (0.5 mole) of 4-methoxycarbonylamino-anthrone in 1.5 liters of water are warmed to 70° C. After adding 50 ml of potassium water glass ($d = 1.25$), 400 ml of a hydrogen peroxide solution which contains 80 g per liter are added dropwise. The mixture is then stirred until the thin layer chromatogram of a sample which is withdrawn indicates the end of the reaction. In the course of the oxidation, the suspension has developed an intense reddish-tinged yellow color. The suspension is filtered and the product is washed until neutral and dried. 130.4 g (= 92.8%) of 1-methoxycarbonylamino-anthraquinone are obtained / melting point 214° C (from nitrobenzene).

EXAMPLE 8

31.3 g (0.1 mole) of 4-benzoylamino-anthrone in 500 ml of water are warmed to 75° C. 10 ml of sodium water glass ($d = 1.35$) are added and 80 ml of an 8% strength hydrogen peroxide solution are then added dropwise. The mixture is kept at 75°-80° C, while stirring, until the thin layer chromatogram of a sample which is withdrawn indicates complete conversion. The mixture is filtered and the product is washed until neutral and dried.

Yield: 29.4 g (= 90.2%) of 1-benzoylamino-anthraquinone / melting point 256° C (from nitrobenzene).

EXAMPLE 9

Air is passed through an intensively stirred suspension of 37.6 g (0.15 mole) of 4-acetamino-anthrone in a mixture of 700 ml of methanol and 45 ml of 10% strength sodium carbonate solution, at 25° to 30° C, until no further starting material is found in the thin layer chromatogram of a sample (running agent THF : toluene = 1: 1 on a silica gel plate). In the course of the oxidation, the initially colorless suspension develops an intense yellow color. 1-Acetamino-anthraquinone, which has precipitated, is filtered off, washed with a little water until neutral and dried.

Yield: 37.6 g (95%) / melting point 212° to 214° C.

EXAMPLE 10

12.55 g (0.05 mole) of 4-acetamino-anthrone, 200 ml of methanol and 10 ml of sodium carbonate solution are filled into an autoclave of 700 ml capacity and pressurized with 20 bars of air at 25° to 30° C. The mixture is stirred for about 1 hour and the pressure is released. 1-Acetamino-anthraquinone is filtered off, washed with a little water until neutral and dried.

Yield: 12.5 g (94.4%) / melting point 214° C.

EXAMPLE 11

134.5 g of 2-acetylamino-2'-carboxy-diphenylmethane are introduced into 220 ml of 100% sulfuric acid; during this addition the temperature should not rise above 30° C. The mixture is stirred for ½ hour at 30° C and 20 ml of 65% strength oleum are then introduced at temperatures between 5° and 20° C. Subsequently, the mixture is warmed to 30° C for 4 hours and is then discharged into a mixture of 590 g of ice and water. The mixture is stirred for a further 1 hour at 20° C and is then filtered. The residue is washed with small amounts of water until neutral and sodium carbonate can be added to the wash water in order to remove the final traces of adhering acids. After drying, 115 g of 1-acetamino-anthraquinone are obtained.

Yield: 91.6% / melting point 266° C.

It will be appreciated that the instant specification and examples are set forth by way of illustration and not limitation, and that various modifications and changes may be made without departing from the spirit and scope of the present invention.

What is claimed is:

1. A process comprising treating a 2-acylamino-2'-carboxy-diphenylmethane with an acid condensing agent, whereby there is formed the corresponding 4-acylamino-anthrone.

2. A process according to claim 1, wherein the acyl radical is derived from a straight-chain or branched aliphatic carboxylic acid having up to 18 carbon atoms, a cycloaliphatic carboxylic acid with 6 to 11 carbon atoms, an araliphatic carboxylic acid with 8 to 10 carbon atoms, an aromatic carboxylic acid with 1 benzene ring or 2 or 3 fused rings and which may be substituted by halogen, nitro, sulfo, alkyl or alkoxy, or an aromatic or aliphatic sulfonic acid.

3. A process according to claim 1, wherein the acid condensing agent is sulfuric acid, chlorosulfonic acid, fluorosulfonic acid, a polyphosphoric acid, a fluoroalkylsulfonic acid or hydrofluoric acid, and the reaction is effected at about 0° to 100° C.

4. A process according to claim 1, wherein the acid condensing agent is employed in about 2 to 10 times the weight of the 2-acylamino-2'-carboxy-diphenylmethane.

5. A process according to claim 1, wherein sulfuric acid is employed as the acid condensing agent and the reaction is carried out at about 20° to 40° C.

6. A process according to claim 1, wherein chlorosulfonic acid is employed as the acid condensing agent and the reaction is carried out at about 0° to 40° C.

7. A process according to claim 1, wherein the 2-acylamino-2'-carboxy-diphenylmethane is 2-acetylamino-2'-carboxy-diphenylmethane.

8. A process according to claim 1, wherein the 2-acylamino-2'-carboxy-diphenylmethane is 2-benzoylamino-2'-carboxy-diphenylmethane.

9. A process according to claim 1, including the further step of oxidizing the 4-acylamino-anthrone, whereby there is formed the corresponding 1-acylamino-anthraquinone.

10. A process according to claim 9, wherein the xoidation is carried out with hydrogen peroxide in the aqueous phase with addition of sodium water glass or potassium water glass.

11. A process according to claim 9, wherein the oxidation is carried out with air or pure oxygen in the alcoholic phase in the presence of an alkaline agent.

12. A process according to claim 9, wherein the 2-acylamino-2'-carboxy-diphenylmethane is 2-acetylamino-2'-carboxy-diphenylmethane whereby the 4-acylamino-anthrone is 4-acetamino-anthrone and the oxidation product is 1-acetamino-anthraquinone.

13. A process according to claim 12, wherein the acid condensing agent is employed in about 2 to 10 times the weight of the 2-acylamino-2'-carboxy-diphenylmethane, the acid condensing agent is sulfuric acid, chlorosulfonic acid, fluorosulfonic acid, a polyphosphoric acid, a fluoroalkylsulfonic acid or hydrofluoric acid, and the reaction is effected at about 0° to 100° C.

* * * * *

UNITED STATES PATENT AND TRADEMARK OFFICE
CERTIFICATE OF CORRECTION

PATENT NO. : 4,062,875
DATED : December 13, 1977
INVENTOR(S) : Horst Jager et al.

It is certified that error appears in the above-identified patent and that said Letters Patent are hereby corrected as shown below:

Column 1, line 37, "[1930, Friedländer 19, 1978].

should be -- [1930, Friedländer 19, 1987]--.

Column 6, line 67 -68, "xoidation" should be

--oxidation--.

Signed and Sealed this

Fourth Day of April 1978

[SEAL]

Attest:

RUTH C. MASON
Attesting Officer

LUTRELLE F. PARKER
Acting Commissioner of Patents and Trademarks